United States Patent [19]

Westcott et al.

[11] Patent Number: 5,705,618

[45] Date of Patent: Jan. 6, 1998

[54] PROCESS FOR EXTRACTING LIGNANS FROM FLAXSEED

[75] Inventors: Neil D. Westcott; Alister D. Muir, both of Saskatoon, Canada

[73] Assignee: Agriculture and Agri-Food Canada, Ottawa, Canada

[21] Appl. No.: 415,050

[22] Filed: Mar. 31, 1995

[51] Int. Cl.[6] .................... C07G 1/00; C08L 97/00
[52] U.S. Cl. .................. 530/500; 530/507; 426/430; 426/479; 426/482; 426/484; 536/4.1; 536/128
[58] Field of Search ................. 530/500, 507; 426/430, 479, 481, 482, 484; 536/4.1, 127, 128

[56] References Cited

U.S. PATENT DOCUMENTS 5,169,660  12/1992  Collins et al. ............... 426/271
5,485,595  1/1996  Ikeya et al. ................. 424/195.1

OTHER PUBLICATIONS

MacRae and Towers, "Biological Activities of Lignans", Phytochemistry, vol. 23, No. 6, pp. 1207-1220, 1984.

Bambagiotti-Alberti et al, "Revealing the Mammalian Lignan Precursor Secoisolariciresinol Diglucoside in Flax Seed by Ionspray Mass Spectrometry", Rapid Communications in Mass Spectrometry, vol. 8, 595-598 (1994).

Primary Examiner—Nathan M. Nutter

[57] ABSTRACT

A process is described for extracting lignans from flaxseed which comprises contacting a substantially oil-free flaxseed meal with an aliphatic alcohol solvent, e.g. a mixture of methanol or ethanol with water, to extract lignans into the alcohol solvent and separating residual solids from the lignan-rich alcohol solvent. The lignan-rich alcohol solvent is concentrated by removing solvent therefrom and the lignan concentrate obtained is subjected to a base-catalyzed hydrolysis to liberate lignans therefrom in a non-complexed form. Thereafter, the hydrolyzed concentrate is subjected to either a liquid/liquid partition, e.g. by an ethyl acetate/water system, or anion exchange to further enrich the lignans and the lignan-enriched solution thus obtained is subjected to chromatographic separation to isolate lignans at a purity of greater than 90 percent. The lignan, secoisolariciresinol diglucoside, was found in amounts of up to 20 mg per gram of defatted flaxseed.

17 Claims, 5 Drawing Sheets

PROCESS FOR EXTRACTING LIGNANS FROM FLAXSEED

BACKGROUND OF THE INVENTION

This invention relates to an improved process for extracting lignans from flaxseed.

Flaxseed is presently grown for its oil content for use primarily as an industrial oil. In addition, flax is a rich source of fatty acids and has increasing uses in foods. Flaxseed suffers from the fact that the level of fatty acid unsaturation in the triglyceride oil is high and is subject to oxidative polymerization.

The scientific literature contains an abundance of reports on the chemistry and physical properties of various components derived from flaxseed. For example, much is known about the feed value of expeller cake meal and its solvent extracted version. The industrial properties of linseed oil are legendary for use in linoleum and paint products. There are also a variety of reports available that describe the extraction and isolation of flaxseed polysaccharides and some suggested uses. Recently, there has been considerable interest shown in a class of minor compounds contained in flaxseed collectively referred to as lignans.

The lignans are generally dimers containing a dibenzylbutane skeleton. When part of the human diet, such compounds are believed to be converted into mammalian lignans known as enterolactone and enterodiol. In a study carried out by Thompson et al (1991) "Mammalian lignan production from various foods", Nutr. Cancer 16:43-52, 68 different primary foodstuffs were surveyed for their ability to produce mammalian lignans. The results revealed that on a per se basis, whole flaxseed flour and its defatted meal were the highest mammalian lignan producers, the meal and flour being 75 times higher than the next ranking entry, a seaweed, and over 100 times greater than most common foodstuffs. The principal lignan found in flaxseed is secoisolariciresinol diglucoside, referred to hereinafter as SDG.

There is considerable published evidence to indicate that lignans as a class of compounds exhibit broad spectrum biological activities that include antitumour, antimitotic, antioxidant, antiviral, weak estrogenic and anti-estrogenic activities. Studies within the chemotherapy program of the National Cancer Institute in the United States indicate that certain of the lignans prevent the growth of tumours.

Thompson et al, "Anticarcinogenic effect of a mammalian lignan precursor from flaxseed", Proc. 55th Flax Institute of U.S.A., Fargo, ND, 46-50 (1994), have studied the effects of SDG on tumorigenesis in rats. When fed in the diet at the promotion stages of tumour formation, SDG can significantly reduce the number of tumours per tumour-bearing rats or per number of rats in the group. At the later stages of mammalian tumorigenesis in rats, SDG can reduce the growth rate of established tumours and the size and number of new tumours formed. Although whole flaxseed or its ground counterpart can be incorporated into foods, the amount or level of usage is restricted by regulation. Furthermore, even if consumption were not regulated, the rather high oil content and the mucilage component of the flax would contribute to excessive caloric intake and excessive laxation respectively.

In a paper by Bakke and Klosterman entitled "A New Diglucoside from Flaxseed", Proceedings of the N. Dakota Academy of Science 10:18-22 (1956), a process is described for extracting SDG from defatted flaxseed using equal parts of 95% ethanol and 1,4-dioxane. Prior publications also refer to methanolysis of complexed SDG (a "polymer") and to the use of a sodium or barium methoxide for methanolysis to release non-complexed SDG.

Harris and Haggerty in an article in Cereal Foods World 38:147-151 (1993) describe the extraction of SDG from defatted flaxseed powder using supercritical fluid carbon dioxide as the extraction medium.

Even though there would appear to be very significant commercial uses for SDG in foods and medicines, the greatest problem has been that even though they have been known for more than 40 years, they are still essentially laboratory curiosities because they are available in only very small quantities. To date, no satisfactory commercial process has been developed for the extraction of lignans, and particularly SDG, from flaxseed. It is, therefore, the main object of the present invention to provide an improved process for extracting lignans from flaxseed which can make lignans available in not only large quantities of high quality but also inexpensively.

SUMMARY OF THE INVENTION

The present invention in its broadest aspect relates to a process for extracting lignans from flaxseed in which a substantially oil-free flaxseed meal is contacted with an aliphatic alcohol solvent to extract lignans into the alcohol solvent. Residual solids are separated from the lignan-rich alcohol solvent and the lignan-rich solvent is then concentrated by removing solvent therefrom. The lignan concentrate thus obtained is subjected to a base-catalyzed hydrolysis in either dry alcohol or an aqueous system to liberate lignans in a non-complexed form. The hydrolyzed concentrate thus obtained from the dry alcohol is subjected to a liquid/liquid partition to further enrich the lignans. The lignan concentrate from the aqueous hydrolysis is subjected to contact with an anion exchange resin to further enrich the lignans. The thus enriched lignans are finally subjected to chromatographic separation to isolate lignans at a purity of greater than 90%.

The aliphatic alcohols used for the initial extraction may be selected from the group consisting of methanol, ethanol, propanol, isopropanol, butanol, etc. Although the alcohols themselves may be used, it has been found that a mixture of alcohol and water is surprisingly superior in its extraction capability. Alcohol mixed with up to 50% water gives the best blend for extraction. Thus, the minimum alcohol concentration is preferably at least 50% with an alcohol content of 65 to 75% being particularly preferred.

Methanol has been found to be the most effective solvent in terms of extraction efficiency. Aqueous ethanol is also highly effective and is preferred from considerations of safety to health and handling.

The alcohol solvent is preferably mixed with the flaxseed meal in a liquid to solids ratio in the range 2:1 to 50:1, with a range of 4-30:1 being particularly preferred. The contact time between the meal and the solvent system is typically in the range of 1 to 24 hours, with a range of 1 to 6 hours being preferred and a range of 1 to 4 hours being most preferred.

While the extraction temperature is not critical, it is most commonly carried out at a temperature between 0° C. and a temperature not exceeding the boiling point of the solvent system of choice. It has been found particularly convenient to carry out the extraction at room temperature.

Following the extraction step, the slurry obtained is subjected to any suitable means of liquid/solid separation as known to those skilled in the art, such as centrifugation, screening, decantation, etc. The residual solids may be further washed with fresh solvent to maximize extraction and the combined liquors may then be filtered by means known to those skilled in the art to produce a liquor free of any suspended solids. The liquor is then concentrated to remove solvent by any of a variety of means known to those skilled in the art, e.g. evaporation under reduced pressure.

In order to isolate the lignans in good yield, the extract is subjected to a base-catalyzed hydrolysis. This hydrolysis may be of either anhydrous or aqueous form.

For the anhydrous system, the extract is concentrated and dried to a generally anhydrous state which may be a thick, syrupy material, e.g. by a technique such as rotary evaporation, freeze-drying, drum-drying, spray-drying, etc. The hydrolysis may then be carried out using a dry alcohol, e.g. dry ethanol or methanol together with a hydrolyzing agent such as sodium methoxide and possibly barium methoxide. This hydrolyzing agent may be added in a typical amount of 0.06–2.5% w/v based on the total volume of liquid. This results in the liberation of lignin plus esters of the corresponding alcohol and other agents which can be difficult to remove. It has also quite surprisingly been found that triethylamine may be effectively used for hydrolysis, e.g. in amounts up to 1.25% w/v based on the total volume of liquid. While it may be possible to use organic amines other than triethylamine, it has been found that triethylamine has important advantages. Thus, it is a medium strength base with a boiling point sufficiently high as not to cause volatility problems during hydrolysis while still being sufficiently low to be removed by traditional evaporative procedures following hydrolysis.

The anhydrous alcohol hydrolysate is subjected to liquid/liquid partitioning and this can be conveniently carried out in a continuous extractor using an ethyl acetate/water solvent system with the ethyl acetate and water preferably being in a ratio in the range of about 1:1 to 7:1. Ethyl acetate is particularly preferred for this purpose because of its polarity. Thus, solvents with polarity below ethyl acetate are unable to effectively remove non-lignan substances from aqueous solutions, which is essential for effective subsequent chromatographic purification of SDG. The non-lignan substances removed in the ethyl acetate fraction may include valuable products, including methyl esters of cinnamic acids and other cinnamic acid derivatives.

For the aqueous base hydrolysis, the extract does not need to be in anhydrous form and may be used in the form of a concentrated syrupy residue. The base is usually selected from ammonium hydroxide, sodium hydroxide and potassium hydroxide, with sodium or potassium hydroxide being preferred. The concentration of, the base is typically about 1 normal and it is preferably used in an amount of about 3–7% w/v. The hydrolysis is normally carried out over about 4 to 24 hours.

The aqueous base hydrolysate contains the SDG, together with other components, and this hydrolysate is contacted with an anion exchange resin. It is necessary to adjust the pH of the hydrolysate to the acidic range, e.g. about pH 3–7, preferably pH 4–6, before contacting the anion exchange resin. This can be done using any suitable inorganic or organic acid, such as hydrochloric acid, sulphuric acid, acetic acid, etc. However, acetic acid is preferred for this purpose.

The anion exchange is preferably carried out in an anion exchange chromatography column prepared in the acetate counterion form. Many different commercially available resins may be used, e.g. A-25 QAE Sephadex®, Q-Sepharose® or DEAE Sephadex®. The acidified hydrolysate is applied to the column and then the column is eluted with water to elute the SDG and some organic and inorganic materials. Further elution of the column with dilute acid, e.g. 50% acetic acid in 15% ethanol elutes acid components which may include valuable products, such as glycosides of cinnamic acids and other cinnamic acid derivatives.

The column may be conveniently regenerated for reuse by means of aqueous sodium hydroxide followed by aqueous acetic acid and finally by water.

The final isolation of lignans at high purity is accomplished by chromatography. Thus, the lignan-rich fraction from the liquid/liquid partitioning or from anion exchange was further purified by contacting a reverse phase resin, e.g. a slurry or column of C18 reverse phase packing. Examples of the C18 reverse phase packing include Radial-Pak® C18, Bondapak® C18 and Nova-Pak® C18, all available from Waters. After the lignan-rich eluant has contacted the resin, the resin is washed with a dilute acid, e.g. 1% acetic acid, to remove organic and inorganic substances and then eluted with aqueous alcohol, e.g. aqueous methanol, to provide an enriched SDG solution.

This enriched SDG solution may then be further processed by preparative high pressure liquid chromatography (HPLC), for example using a C18 reverse-phase column support and an elution system consisting of water/acidic acid/methanol under gradient conditions of 100% aqueous acidic acid to 40% aqueous acidic acid/60% methanol. The lignans thus eluted were found to be purified to a level of greater than 90% in terms of physical, spectral and structural analysis consistent with known literature values.

Employing this strategy as a screening tool, it has been possible to detect the flaxseed lignan, SDG, in amounts of up to 20 mg per gram of defatted flaxseed. This represents up to a 6,000 fold increase in yield over previously known techniques as described in the published literature.

DESCRIPTION OF THE PREFERRED EMBODIMENTS

Example 1

Substantially oil-free flaxseed meal was obtained from CanAmera Foods (Attona, MB). The meal had been commercially crushed and solvent extracted. A 0.5 kg sample of meal was extracted at room temperature by intermittent slurrying with a mixture of 70% ethanol and 30% water in a liquid:solids ratio of 6:1. After 24 hours the suspension was filtered and the extract was evaporated under reduced pressure to produce a syrupy concentrate which was further dried to form a dry extract. The dried extract was then subjected to a base-catalyzed hydrolysis using triethylamine in anhydrous methanol in a ratio of 1:100.

The hydrolysate that was obtained from triethylamine catalysis was then subjected to liquid/liquid partitioning using ethyl acetate/water in the ratio 4:1. The ethyl acetate phase containing methyl esters and other ethyl acetate solubles was concentrated under reduced pressure, and the aqueous phase containing SDG was freed of ethyl acetate by concentration under reduced pressure. The SDG containing fraction was further purified by contacting Radial-Pak C18 reversed phase resin packed in a low pressure column. After the SDG containing fraction had contacted the resin, the column was washed with 1% acetic acid to remove unspecified organic and inorganic substances. Thereafter, the column was eluted with an aqueous solution of 1% acetic acid in 30% methanol to remove a SDG enriched fraction that was concentrated under reduced pressure. The purity of SDG was greater than 60% by weight.

The SDG separated fraction was then subjected to preparative scale high pressure liquid chromatography (HPLC) using a column packed with C18 reverse phase resin, e.g. Radial-Pak® C18 packing (Waters Chromatography). The eluting system consisted of water/acetic acid/methanol under gradient conditions of 100% aqueous acetic acid to 40% aqueous acetic acid/60% methanol. The eluants contained lignans at a purity of greater than 90%.

Figure 1:
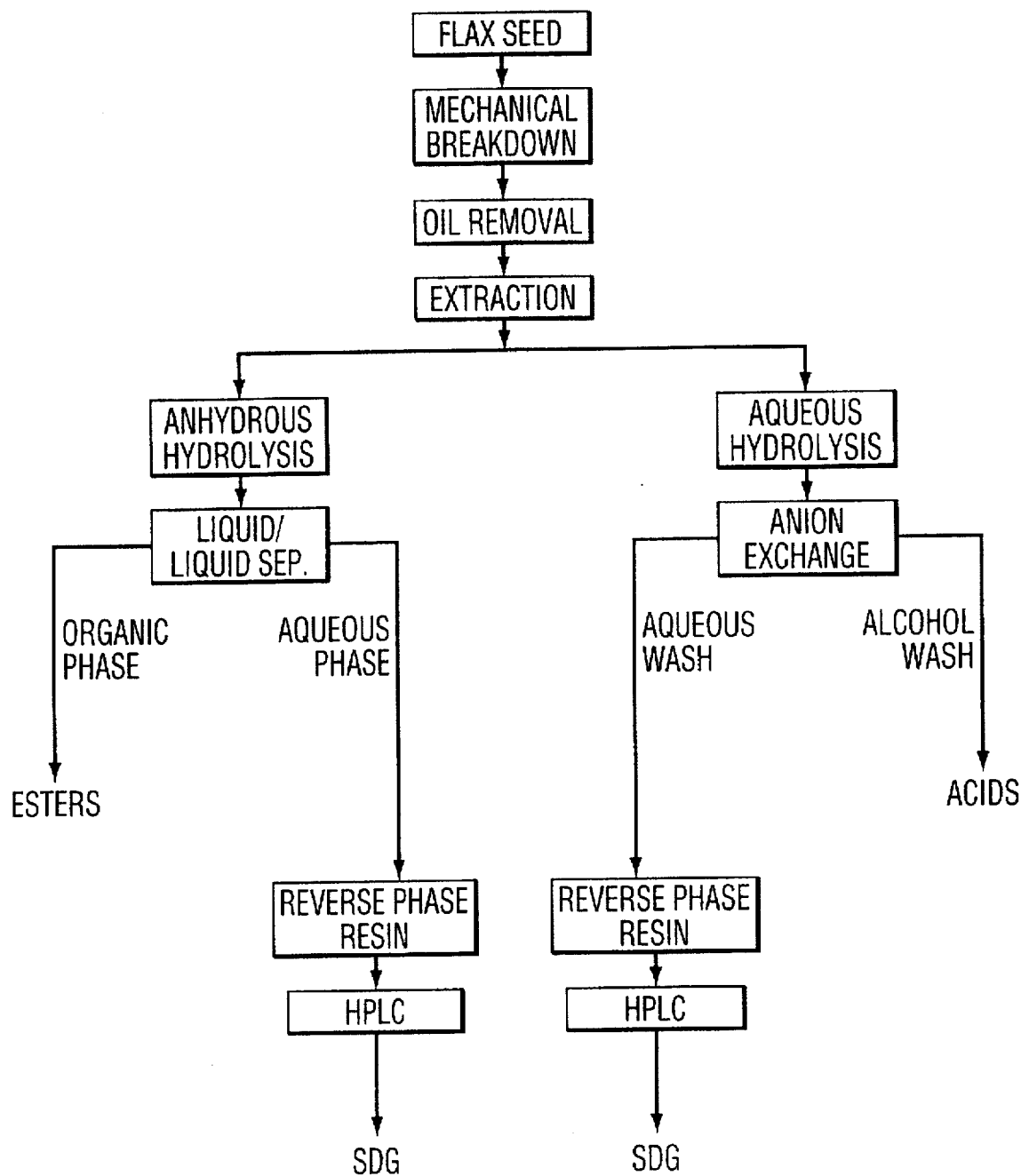
FIG. 1 is a preferred flowsheet of the new process.
Figure 2:
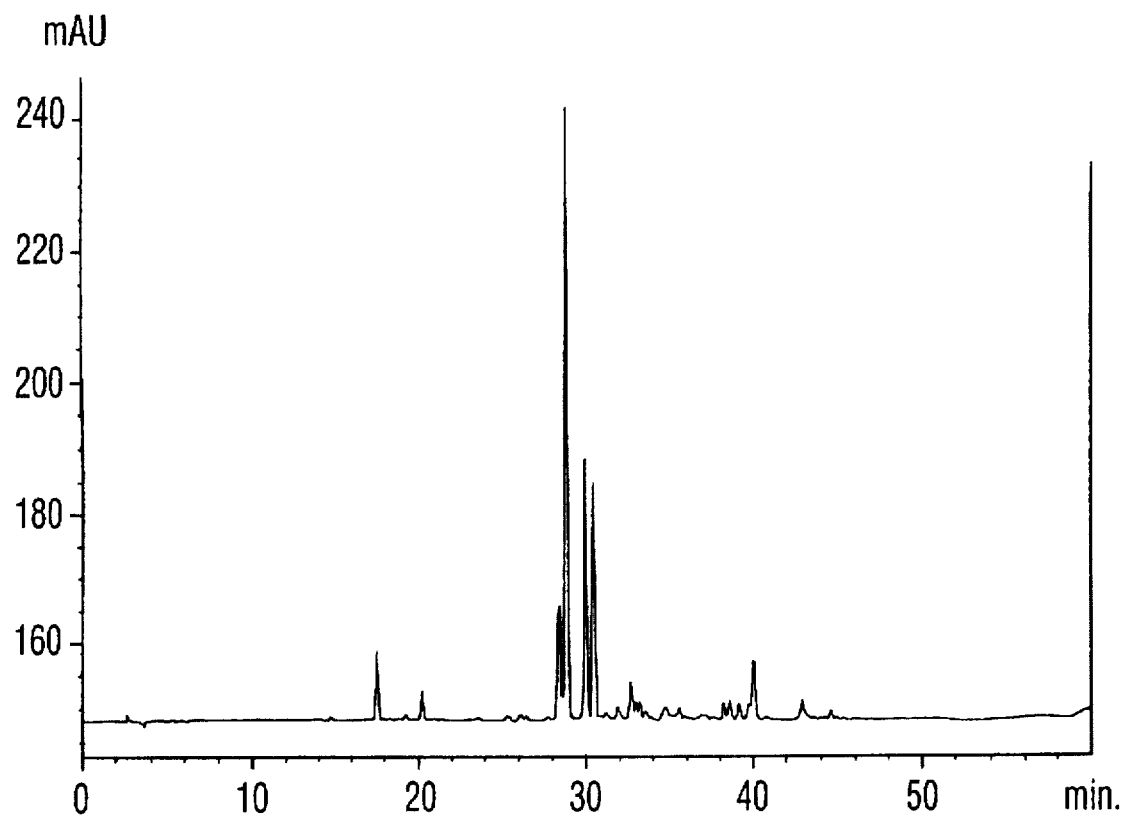
FIG. 2 is a chromatogram of a triethylamine hydrolysate of an alcoholic extract of flaxseed meal.
Figure 4:
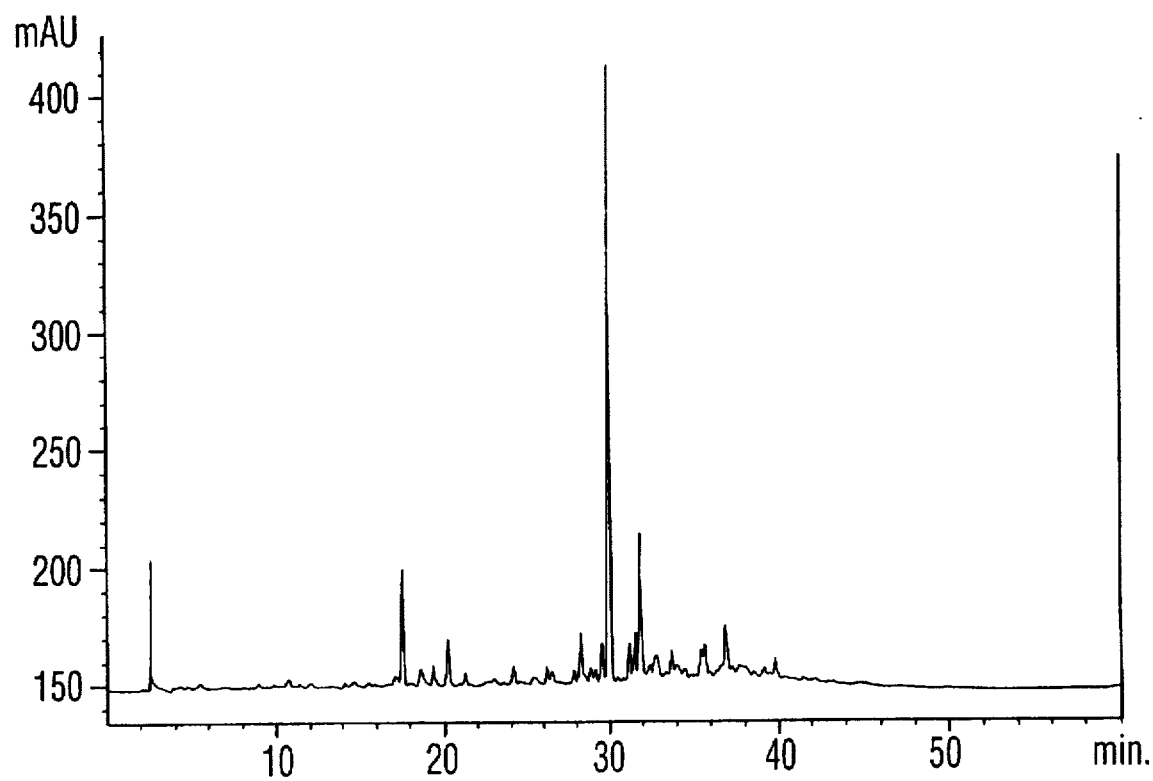
FIG. 4 is a chromatogram of the aqueous (SDG) fraction after ethyl acetate extraction of triethylamine hydrolysate.
Figure 5:
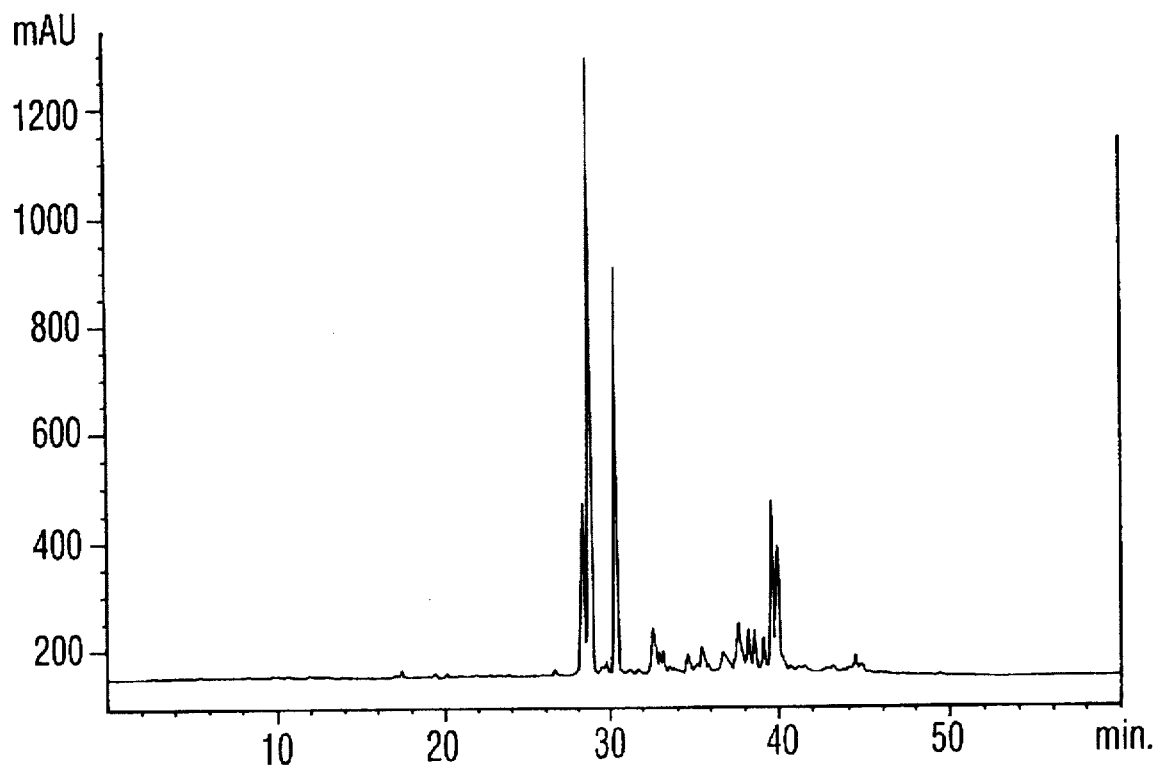
FIG. 5 is a chromatogram of the ethyl acetate fraction after ethyl acetate extraction of triethytamine hydrolysate.
Figure 8:
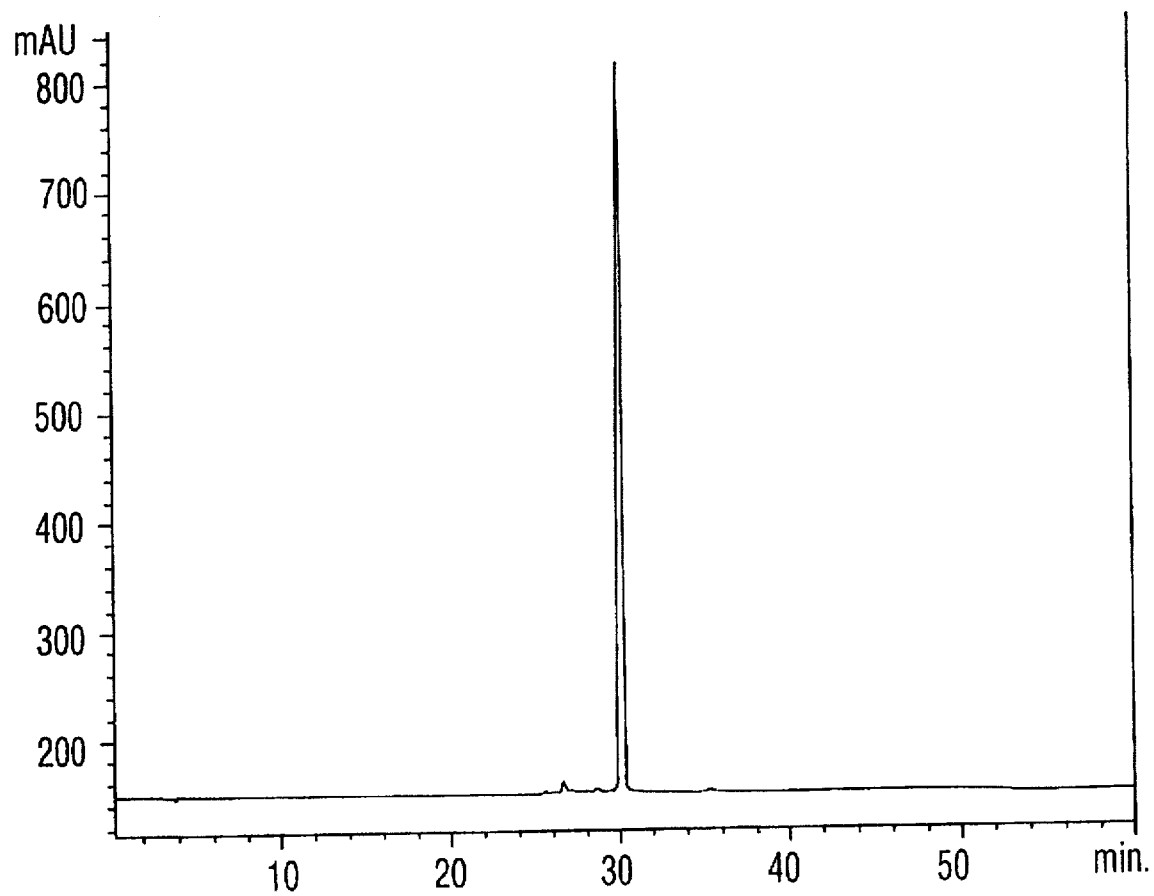
FIG. 8 is a chromatogram of SDG after HPLC purification.

FIG. 2 shows a chromatogram for a triethylamine hydrolysate, FIG. 4 shows a chromatogram of the aqueous phase after ethyl acetate extraction, FIG. 5 shows the ethyl acetate phase of the extraction, while FIG. 8 shows a chromatogram of the purified SDG. These show the effectiveness of the ethyl acetate and reverse phase resins in separating SDG from co-extractives thereby simplifying the isolation and purification.

Example 2

Substantially oil-free flaxseed meal was obtained from CanAmera Foods (Attona, MB). The meal had been commercially crushed and solvent extracted. A 0.5 kg sample of meal was extracted at room temperature by intermittent slurrying with a mixture of 70% ethanol and 30% water in a liquid:solids ratio of 6:1. After 24 hours the suspension was filtered and the extract was evaporated under reduced pressure to produce a syrupy concentrate.

The concentrate was then subjected to base-catalyzed hydrolysis using sodium hydroxide in water in a ratio of 5:100. The pH of the hydrolysate that was obtained from sodium hydroxide hydrolysis was adjusted to 5 using acetic acid and the aqueous phase so obtained contacted A-25 QAE Sephadex anion exchange resin in a column prepared in the acetate counterion form. Thereafter, the column was eluted with water to elute the SDG and unspecified organic and inorganic substances. The column was then further eluted with 50% acetic acid in 15% ethanol, to obtain an eluant containing acid components, including glycosides of cinnamic acids and other cinnamic acid derivatives.

The SDG containing fraction was further purified using Radial-Pak C18 reverse phase resin in the same manner as in Example 1. The SDG enriched fraction thus obtained was then subjected to preparative scale high pressure liquid chromatography using a column packed with C18 reverse phase resin in the same manner as in Example 1, to obtain eluants containing lignans at a purity of greater than 90%.

Figure 3:
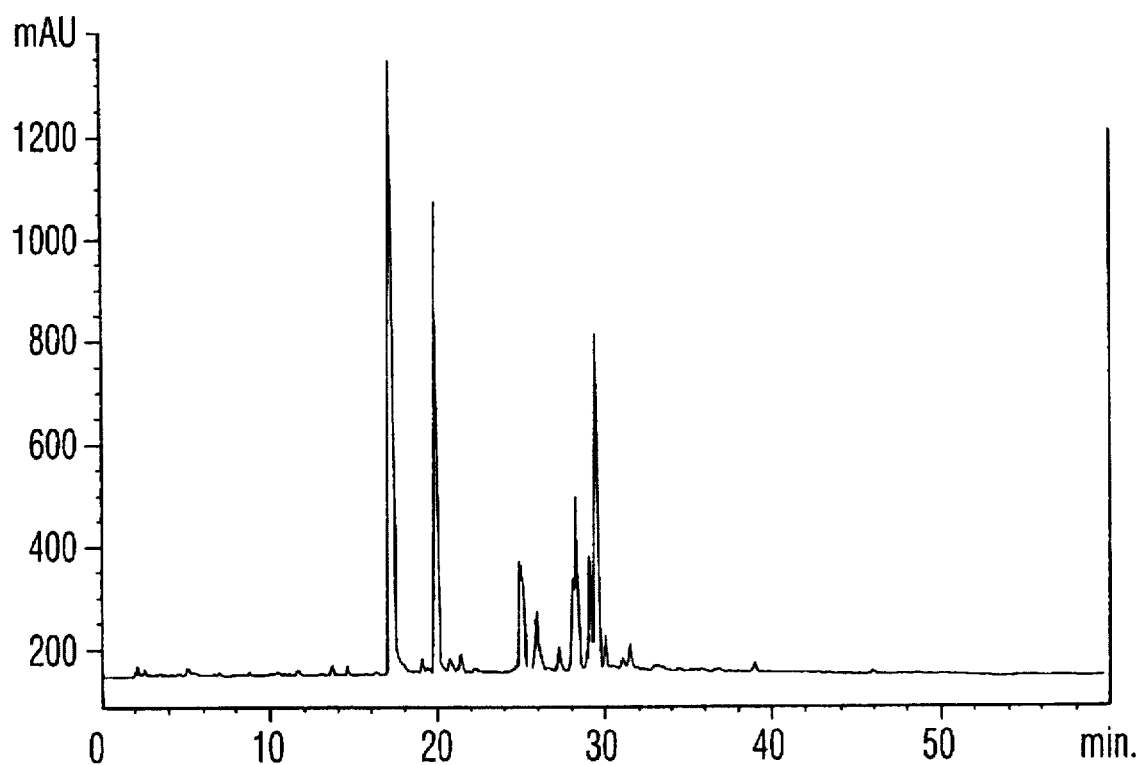
FIG. 3 is a chromatogram of a sodium hydroxide hydrolysate of an alcoholic extract of flaxseed meal.
Figure 6:
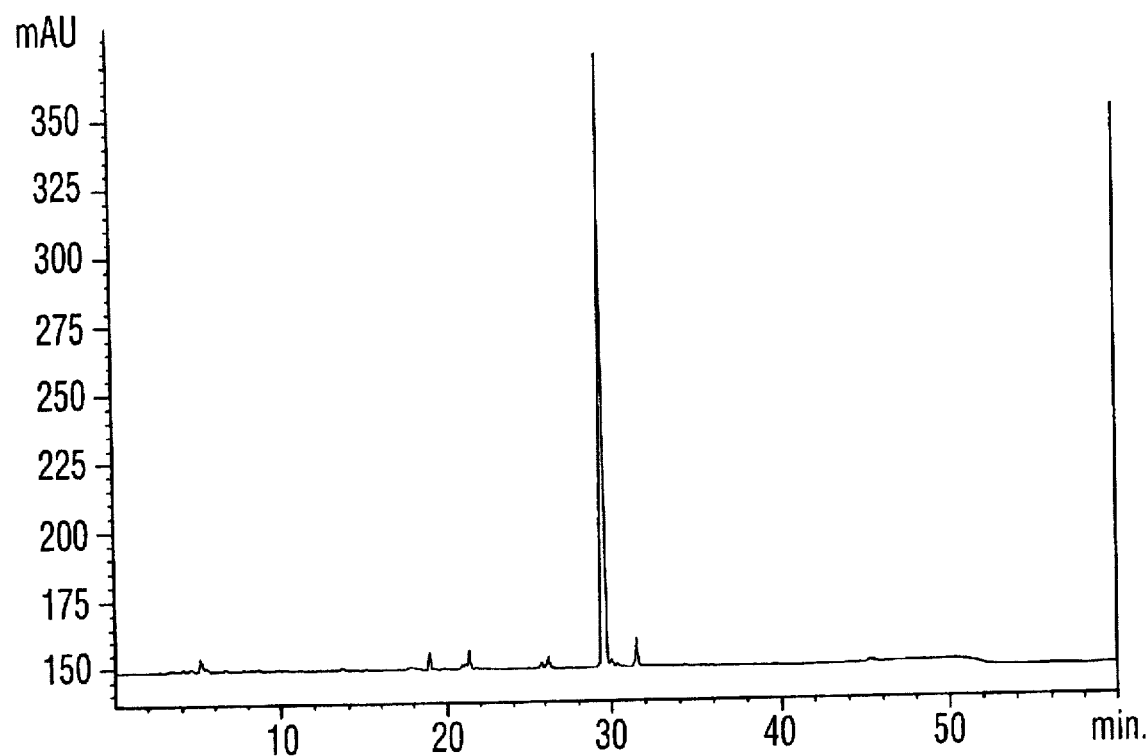
FIG. 6 is a chromatogram of the aqueous (SDG) wash after anion exchange of the sodium hydroxide hydrolysate.
Figure 7:
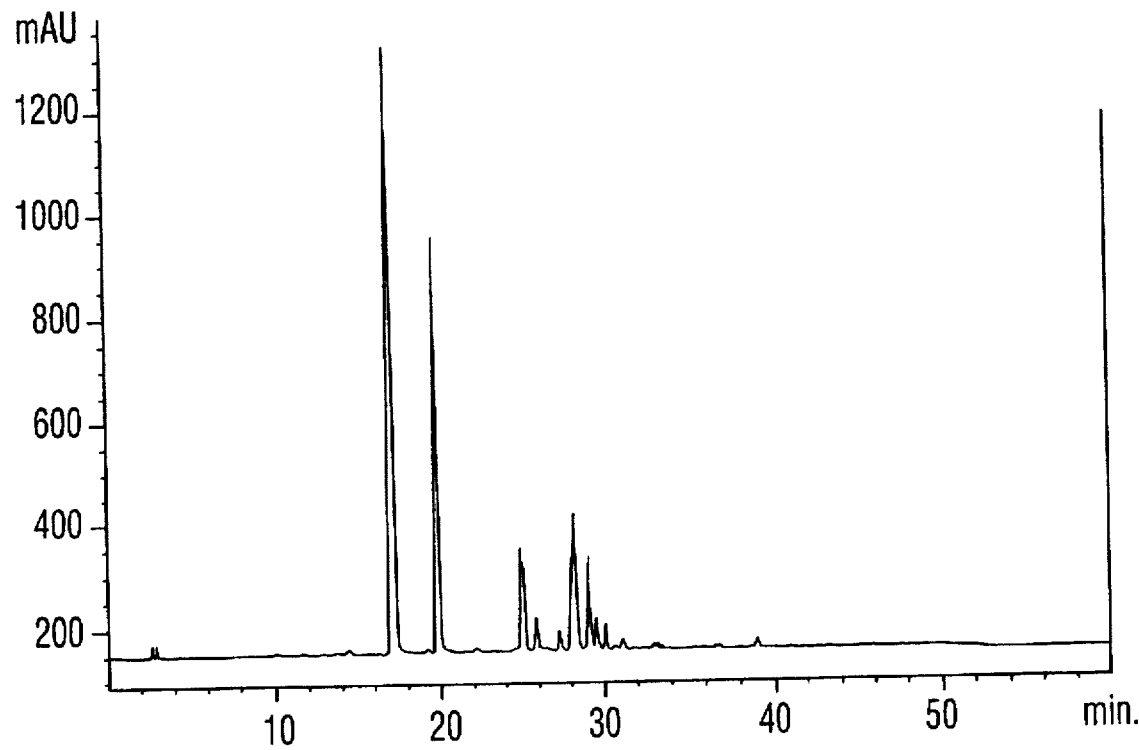
FIG. 7 is a chromatogram of the alcoholic wash after anion exchange of the sodium hydroxide hydrolysate.

FIG. 3 shows a chromatogram for an aqueous sodium hydroxide hydrolysate, FIG. 6 shows a chromatogram of the aqueous (SDG) wash after anion exchange of the sodium hydroxide hydrolysate, FIG. 7 shows a chromatogram of an aqueous alcoholic wash after anion exchange of the sodium hydroxide hydrolysate, while FIG. 8 shows a chromatogram of the purified SDG after HPLC purification. These show the effectiveness of the anion exchange and reverse phase resins in separating SDG from co-extractives thereby simplifying the isolation and purification.

We claim:

1. A process for extracting lignans and/or cinnamic acid derivatives from flaxseed which comprises contacting a substantially oil-free flaxseed meal with an aliphatic alcohol solvent to extract phenolics comprising secoisolariciresinol diglucoside (SDG) and cinnamic acid derivatives into the alcohol solvent, separating residual solids from the phenolic-rich alcohol solvent, subjecting the phenolic-rich alcohol extract obtained to an aqueous base-catalyzed hydrolysis to liberate SDG and cinnamic acid derivatives therefrom in a non-complexed form.

2. A process according to claim 1 wherein the aliphatic alcohol solvent is a mixture of said alcohol and water.

3. A process according to claim 2 wherein the alcohol is selected from methanol and ethanol.

4. A process according to claim 1 wherein the base-catalyzed hydrolysis is carried out by mixing the phenolic-rich alcohol extract with aqueous alkali metal hydroxide.

5. A process according to claim 4 wherein the phenolic-rich alcohol extract is concentrated by removal of solvent.

6. A process according to claim 4 wherein the aqueous base hydrolysate obtained containing SDG is contacted with an anion exchange resin, after which the resin is eluted with water to elute the SDG together with some organic and inorganic materials.

7. A process according to claim 6 wherein the aqueous base hydrolysate is neutralized to a pH in the range 3–7 before contacting the anion exchange resin.

8. A process according to claim 6 wherein the eluate containing SDG is further enriched in SDG by contacting with a reverse-phase resin, after which the resin is eluted with a dilute acid/alcohol gradient to obtain SDG at a purity greater than 90 percent.

9. A process according to claim 6 wherein after the resin is eluted with water to elute the SDG, it is further eluted with a dilute acid to remove a separate product containing glycosides of cinnamic acids and other cinnamic acid derivatives.

10. A process according to claim 4 wherein the aqueous base hydrolysate obtained containing SDG is contacted with a C-18 reverse-phase solid phase extraction resin at pH 3–5, after which the resin is washed with dilute acid and eluted with alcohol.

11. A process according to claim 10 wherein the alcohol eluate from the C-18 reverse-phase solid phase extraction resin is further contacted with a C-18 reverse-phase solid phase extraction resin equilibrated in water, after which the resin is washed with water and dilute alcohol to recover the cinnamic acid glycosides, and the resin eluted with alcohol or an alcohol water mixture to recover the SDG.

12. A process for extracting lignans and/or cinnamic acid derivatives from flaxseed which comprises contacting a substantially oil-free flaxseed meal with an aliphatic alcohol solvent to extract phenolics comprising secoisolariciresinol diglucoside (SDG) and cinnamic acid derivatives into the alcohol solvent, separating residual solids from the phenolic-diglucoside (SDG) and cinnamic acid derivatives into the alcohol solvent, separating residual solids from the phenolic-rich alcohol solvent and removing solvent to obtain a phenolic-rich alcohol extract in dry form, subjecting the dry phenolic-rich extract to an anhydrous base-catalyzed hydrolysis to obtain a hydrolyzed anhydrous concentrate containing SDG and cinnamic acid derivatives in a non-complexed form and subjecting the hydrolyzed anhydrous concentrate obtained to liquid/liquid partition using an ethyl acetate/water system whereby SDG is isolated in the aqueous phase and cinnamic acid derivatives are in the ethyl acetate phase.

13. A process according to claim 12 wherein the base-catalyzed hydrolysis is carried out by slurrying the dried extract in anhydrous ethanol or methanol and in the presence of sodium alkoxide or triethylamine.

14. A process according to claim 13 wherein the base catalyzed anhydrous hydrolysate obtained containing SDG is contacted with an anion exchange resin, after which the resin is eluted with water to elute the SDG together with some organic and inorganic materials.

15. A process according to claim 12 wherein the aqueous phase from the liquid/liquid partition is further enriched in SDG by contacting with a reverse phase resin.

16. A process according to claim 14 wherein a separate product containing esters of cinnamic acid glycosides and other cinnamic acid derivatives is removed in the ethyl acetate fraction.

17. A process according to claim 13 wherein the anhydrous base hydrolysate obtained containing SDG is contacted with a C-18 reverse-phase solid phase extraction resin at pH 3–5, after which the resin is washed with dilute acid and eluted with alcohol to elute the SDG together with some organic materials.

* * * * *